(12) United States Patent
Srinivasan et al.

(10) Patent No.: US 9,144,389 B2
(45) Date of Patent: Sep. 29, 2015

(54) SYSTEM FOR VEHICLE SECURITY, PERSONALIZATION AND CARDIAC ACTIVITY MONITORING OF A DRIVER

(75) Inventors: Jayaraman Srinivasan, Bangalore (IN); Venkatesh Narasimha Murthy, Bangalore (IN); Balamuralidhar Purushothaman, Bangalore (IN)

(73) Assignee: TATA CONSULTANCY SERVICES LIMITED, Mumbai, Maharashtra (IN)

( * ) Notice: Subject to any disclaimer, the term of this patent is extended or adjusted under 35 U.S.C. 154(b) by 73 days.

(21) Appl. No.: 13/380,137

(22) PCT Filed: Aug. 31, 2010

(86) PCT No.: PCT/IN2010/000581
§ 371 (c)(1),
(2), (4) Date: Dec. 22, 2011

(87) PCT Pub. No.: WO2011/111056
PCT Pub. Date: Sep. 15, 2011

(65) Prior Publication Data
US 2012/0101690 A1    Apr. 26, 2012

(30) Foreign Application Priority Data

Mar. 12, 2010   (IN) .......................... 658/MUM/2010

(51) Int. Cl.
*A61B 5/00* (2006.01)
*A61B 5/0408* (2006.01)
(Continued)

(52) U.S. Cl.
CPC ............. *A61B 5/0408* (2013.01); *A61B 5/6887* (2013.01); *G07C 9/00563* (2013.01); *B60W 2040/0872* (2013.01); *B60W 2540/22* (2013.01); *B60W 2540/28* (2013.01)

(58) Field of Classification Search
CPC .. A61B 5/0022; A61B 5/0024; A61B 5/0015; G08C 17/02; G06F 19/3418
USPC ............ 340/12.53, 426.24, 426.25, 435, 438, 340/439, 2.53; 701/1, 49; 706/20; 713/166, 713/186; 715/790
See application file for complete search history.

(56) References Cited

U.S. PATENT DOCUMENTS 3,731,672 A    5/1973   Mcintosh
4,706,072 A   11/1987   Ikeyama
(Continued)

FOREIGN PATENT DOCUMENTS

DE    10310719 A1    9/2004
EP    1477370 A2    11/2004
(Continued)

OTHER PUBLICATIONS

Andreas Riener, Alois Ferscha, and Michael Matscheko "Intelligent Vehicle Handling: Steering and Body Postures While Cornering" .
(Continued)

*Primary Examiner* — Tuan C. To
*Assistant Examiner* — Jelani Smith
(74) *Attorney, Agent, or Firm* — Thompson Hine LLP (57) ABSTRACT

The present invention provides a system for vehicle security, personalization, and cardiac activity monitoring of a driver wherein electrocardiography of a driver is monitored and registered which is used for identification of a person entering in the vehicle and personalization of vehicle based on user preferences thereby act as intruder detection towards vehicle security. In addition to registration the present invention also monitors cardiac activity of driver in a continuous and real time fashion without any intrusion to driver with the facility of generation of alert and making emergency call.

12 Claims, 5 Drawing Sheets

(51) Int. Cl.
  *G07C 9/00* (2006.01)
  *B60W 40/08* (2012.01)

(56) References Cited

U.S. PATENT DOCUMENTS

| | | | |
|---|---|---|---|
| 5,574,641 | A | 11/1996 | Kawakami et al. |
| 5,735,799 | A * | 4/1998 | Baba et al. ............... 600/500 |
| 5,783,997 | A | 7/1998 | Saitoh et al. |
| 6,104,296 | A | 8/2000 | Yasushi et al. |
| 6,217,525 | B1 * | 4/2001 | Medema et al. ........... 600/508 |
| 6,575,902 | B1 | 6/2003 | Burton |
| 6,599,243 | B2 | 7/2003 | Woltermann et al. |
| 6,600,430 | B2 * | 7/2003 | Minagawa et al. ......... 340/988 |
| 6,603,999 | B2 * | 8/2003 | SerVaas ....................... 607/5 |
| 7,223,204 | B2 * | 5/2007 | Steen et al. ................. 477/97 |
| 7,605,694 | B2 * | 10/2009 | Prost-Fin et al. ........... 340/438 |
| 7,774,052 | B2 * | 8/2010 | Burton et al. .............. 600/544 |
| 7,945,313 | B2 * | 5/2011 | Fuwamoto et al. ......... 600/509 |
| 8,108,083 | B2 * | 1/2012 | Kameyama ................... 701/1 |
| 8,169,305 | B2 * | 5/2012 | Matsumoto et al. ...... 340/384.1 |
| 8,344,849 | B2 * | 1/2013 | Larsson et al. ............. 340/5.2 |
| 2003/0097047 | A1 | 5/2003 | Woltermann et al. |
| 2008/0252412 | A1 * | 10/2008 | Larsson et al. ............. 340/5.2 |
| 2009/0234262 | A1 | 9/2009 | Reid, Jr. et al. |
| 2010/0076333 | A9 * | 3/2010 | Burton et al. .............. 600/544 |
| 2010/0322294 | A1 * | 12/2010 | Park et al. .................. 375/219 |
| 2012/0179008 | A1 * | 7/2012 | Burton ....................... 600/301 |
| 2014/0055284 | A1 * | 2/2014 | Tran et al. ............... 340/870.07 |

FOREIGN PATENT DOCUMENTS

| | | |
|---|---|---|
| WO | 01/24700 A1 | 4/2001 |
| WO | 2006/048701 A2 | 5/2006 |

OTHER PUBLICATIONS

Keith Baker, Emre Kucukayvaz, Ozgun Algin "Role of Nomadic Devices Coupled to In-Cockpit Wireless Networks for the eCall System: Quo Vadis".

Chaikowski I et al: "Value of the single-lead ECG in comparison with 12-lead ECG" Jan. 1, 2008, vol. 6, No. 1, pp. 25-27,XP007917364.

Andreas Riener et al "Heart on the road: HRV analysis for monitoring a driver's affective state" Proceedings of the First International Conference on Automotive User Interfaces and Interactive Vehicular Applications (Automotiveui 2009), Sep. 21-22, 2009, Essen, Germany, ACM, Association for Computing Machinery, Sep. 21, 2009, pp. 99-106, XPOO7917365, ISBN:978-1-61738-615-2 Paragraphs [02.2], [03.03] figure 1.

John M Irvine and Steven A Israel: "A Sequential Procedure for Individual Identity Verification using ECG" Eurasip Journal on Advances in Signal Processing, Hindawi Publishing Corp, US, vol. 2009, Jan. 1, 2009.

Hee-Soo Park et al "ECG Pattern Classification Based on Generic Feature Extraction" Proceedings of the 3rd WSEAS Int. Conf. on Circuits, Systems, Signal and Telecommunications (CISST'09).

* cited by examiner

SYSTEM FOR VEHICLE SECURITY, PERSONALIZATION AND CARDIAC ACTIVITY MONITORING OF A DRIVER

FIELD OF INVENTION

The present invention relates to a system for vehicle security, personalization and monitoring cardiac activity of a driver. More particularly the invention relates to a use of integrated ECG (electrocardiography) device in vehicles for recording and storing electrical signals generated by cardiac muscles of driver and to monitor the cardiac condition of the driver. In addition to this, the present invention also relates to a means for person identification and associating a person with a particular vehicle using acquired ECG signal to actuate personalization of vehicle, and act as person identification basis, to prevent the unauthorized access to the vehicle.

BACKGROUND OF THE INVENTION

Cardiac diseases are one of the leading causes of death in the western countries and due to stressful lifestyle are alarmingly increasing in Asian and South Asian counties as well. The majority of cardiac deaths are sudden, and nearly half of the cardiac deaths occur outside hospitals. Staggeringly, 63.4% of heart disease deaths that occurred fall into the category of sudden cardiac death. In addition, 46.9% of heart disease patients who died, did so before reaching the hospital, while another 16.5% were pronounced dead on arrival or died immediately upon arrival in the emergency room. In fact, cardiac disease is the leading cause of death in the developed countries as well as in most of the emerging nation. Studies indicate that approximately 70% of the people who die of cardiac diseases are not diagnosed until their death. These studies demonstrate that all patients with diagnosed cardiac disease and people with high risk of cardiac disease would benefit by being monitored for early detection of cardiac abnormalities. Interestingly, most of the cardiac abnormalities, in many cases are transient and can be avoided if detected at an early stage. (Chaikowski et al. *z. telemed med. telemat*.-2008.-Vol. 6, No 1.-P.25-27).

Vehical driving is affected by an increasing number and complexity of Driver Assistance Systems (DAS), resulting in a raised cognitive load of a driver. Consequently, these DASs add to the distraction from the main activity of driving (Riener et al., 2009). A number of potential solutions have been proposed so far, however, these techniques broaden the perception horizon of a driver e.g. the introduction of the sense of touch as additional information modality or the utilization of multimodal instead of unimodal interfaces. These solutions demand attention of the driver. In order to cope with the issues of workload and/or distraction, it is essential to find a non-distracting and noninvasive solution for generation of significant sensory information about the driver's awareness and health condition.

For many of the above stress monitoring systems it is also expected to confirm the identity of the driver to avoid an unauthorized access to a vehicle and thus enable decision making for alert generation. There are biometric techniques for disclosing the identity of the driver to the car. Fingerprint is one of the most popular methods. Recently it has been shown that ECG can be used as a biometric input for person identification. The work in (Irvine et al., 2009, EURASIP Journal on Advances in Signal Processing Volume 2009, Article ID 243215, 13 pages) describes the results of such an experimentation of using ECG as a biometric.

Some of the inventions which deal in cardiac monitoring in vehicle are as follows:

US20070265540 discloses a heart-rhythm monitoring device for a vehicle which determines whether a driver has an arrhythmia while driving the vehicle or not.

U.S. Pat. No. 5,574,641 discloses an apparatus and method to monitor heartbeat pulse information for improving the awareness of vehicle drivers by prompting the vehicle driver when it is determined that the awareness of the vehicle driver is decreasing due to the driver falling asleep. However, it failed to disclose the ECG monitoring and secure biometric identification of the driver with display of ECG waveform along with heart rate.

U.S. Pat. No. 4,706,072 discloses a human condition and security controlling apparatus on road-vehicles for detecting the condition of a driver by measuring fluctuation in heart rate and taking a given security action in accordance with the detected result but it failed to disclose ECG monitoring and biometric identification of driver.

U.S. Pat. No. 6,599,243 discloses a system for advising or averting potentially dangerous driving situations based on an analysis of driver stress but it failed to disclose display of health status or ECG waveform and generation of alert with the facility of making E-call in case of emergency.

U.S. Pat. No. 5,783,997 discloses a cardiac rate measuring apparatus which measures the cardiac rate of a driver without restraining motions of the driver and U.S. Pat. No. 6,575,902 discloses a system for monitoring, recording and/or analyzing vigilance, alertness or wakefulness and/or a stressed state of an operator of equipment or machinery but both failed to disclose ECG monitoring and biometric identification of the driver with display of ECG waveform along with heart rate and also facility of making emergency call.

However, all the above mentioned inventions do not provide personalization of vehicle and identification of driver by using Electrocardiography.

In order to overcome the above mentioned drawbacks in the prior art, the present invention provides an integrated the ECG sensing device in vehicle for vehicle security, personalization and monitoring the heart status.

OBJECT OF INVENTION

The principle object of the present invention is to provide a system for vehicle security, personalization and monitoring cardiac activity of a driver in a vehicle.

Another object of the present invention is to monitor cardiac status of driver in a continuous and real-time fashion.

Yet another object of the invention is to provide a solution for person identification using ECG trace recorded by cardiac device installed in vehicle.

Still another object of the invention is to provide a device to display the ECG trace, Heart rate, Sound track.

Further object of the present invention is to provide automatic personalization of the vehicle on the basis of the registered biometric profile of the drivers wherein the personalization scheme comprises re-setting of the rear view mirrors, active play list of songs, video and FM/TV stations, speaker volume, sound level of horn, dashboard display, perfume fragrance, seat height, tilt, climate control settings, speed limit, security settings, navigation display settings, engine response etc.

Another object of the invention is to provide real-time diagnosis of cardiac activity of vehicle driver wherein in case of an emergency an automatic emergency call or alert can be generated by the system.

Another object of the present invention is to provide vehicle security by preventing unauthorized access of the vehicle.

Yet another object of the invention the cardiac activity is monitored using non intrusive biosensors.

Yet another object of the invention is to use the ECG based driver identity as information to assign responsibility or to ensure identity of the driver in case of accidents.

Another object of the invention is to provide a scheme for privacy enabled handling of ECG data captured.

SUMMARY OF THE INVENTION

The present invention provides a system for vehicle security, personalization and monitoring cardiac activity of a driver wherein the system comprises non intrusive biosensors placed inside the vehicle for monitoring the real time electrical signal generated by cardiac muscles of the driver. The system conceptualized by the inventors of this invention also in case of an emergency generate an automatic emergency call or alert in case of abnormal cardiac condition. The present invention also discloses the use of acquired ECG signal (from the biosensors placed either inside or outside of the vehicle) as a secure biometric system for person identification so that person identification information can be used for authentication and personalization of in-vehicle security and infotainment services.

BRIEF DESCRIPTION OF DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any methods or system or equivalent to those described herein can be used in the practice or testing of embodiments of the present invention, the preferred methods and system are now described. The invention is further described in detail in the following paragraphs, which are given by way of illustration. The scope of the present invention is intended to be limited by only by the claims and its equivalents.

The following paragraphs describe a few illustrative embodiments of the invention that exemplify some of its aspects and features. They are not exhaustive in illustrating its many aspects and embodiments, and thus are not in any way limitative of the invention. Many other aspects, features, and embodiments of the invention are described herein. Many other aspects and embodiments will be readily apparent to those skilled in the art upon reading the application and giving it due consideration in the full light of the prior art and knowledge in the field.

The present invention provides a non-distracting and non-invasive, in-vehicle system for identification, personalization, and monitoring cardiac activity of a driver in a vehicle based on ECG data wherein the system comprises:

a. plurality of ECG trace probing means, each means being a sensor mounted on one or more parts of the vehicle for acquiring in real-time an electric signal generated by cardiac muscles of driver;

b. a means for extracting ECG features and one time enrolling of ECG trace as binary code sequence using processor implemented binary sequence code book generation algorithm in a binary code book based on the ECG data of the driver captured from the said probing means;

c. a means for detecting and allowing the entry of the driver in the vehicle wherein the binary code of the driver's ECG trace is matched with the registered binary code book sequence using processor implemented steps of nearest neighbor classifier algorithm;

d. a means for storing driver's preferences for personalization in vehicle wherein the triggering of personalization occurs after matching the driver's ECG features and binary code with registered binary code book sequence;

The present invention also provides a system for vehicle security to detect unauthorized access of the vehicle wherein the system comprises:

a means for extracting ECG features and one time enrolling of ECG trace as binary code sequence using processor implemented binary sequence code book generation algorithm in a binary code book based on the ECG data of the driver captured from the said probing means;

a means for detecting and allowing the entry of the driver in the vehicle wherein the binary code of the driver's ECG trace is matched with the registered binary code book sequence using processor implemented steps of nearest neighbor classifier algorithm.

According to one of the embodiments of the present invention, a vehicle biosense cardiac monitoring device is a miniature device which measures the single lead 1 lead electrocardiogram (ECG) signal which can be integrated to various vehicular parts where a non intrusive personal access is possible to acquire signal ECG like steering wheel, seat, gear shift lever etc. Lead is an electrical picture of the heart. ECG recorder compares the electrical activity detected in the different electrodes and the electrical picture so obtained is called lead.

According to one of the preferred embodiments of the invention there is a means for registering one time the driver's biometric profile which includes ECG waveform, heart rate etc which detects the unauthorized entry of a person in a vehicle.

In one embodiment of the invention the secured biometric system has been achieved by storing the individual's data as binary code sequence. Binary code sequences were generated from the extracted feature of the ECG trace based on Binary code book rules which accounts for feature variance.

In a preferred embodiment of the invention the system generates appropriate alerts (50) if person's profile does not match with the registered profile. This can be used as one of the features for intruder detection towards vehicle security for which the deployment of the ECG can be placed on door handle or steering wheel.

According one preferred embodiment of the present invention there is also a means for storing the driver's preferences for personalization of vehicle which includes but is not limited to the following: Re-setting of the rear view mirrors, active play list of songs, video and fm/television stations, speaker volume, sound level of horn, dashboard display, perfume fragrance, seat height, tilt, climate control settings, speed limit, security settings, navigation display settings, engine response etc. This is not an exhaustive list and the invention need not be bound by limitations set forth herein, and the invention can include all automatically configurable settings in the vehicle as per user preferences. Still in another embodiment of the present invention, identification of the person or driver inside the vehicle triggers personalization of the vehicle through automatic re-configuration guided by user profile or preferences which are being already set by driver/user.

In an another embodiment of the invention the biometric profile and personalization settings of different driver can be stored, and system will detect the identity and personalization scheme by matching already registered profile with the ECG and biometric profile of the person entering in the vehicle. If profile does not match, the system will generate an alert to a concerned person and thereby the system as proposed in this invention also acts as intruder detector towards vehicle security.

Figure 1:
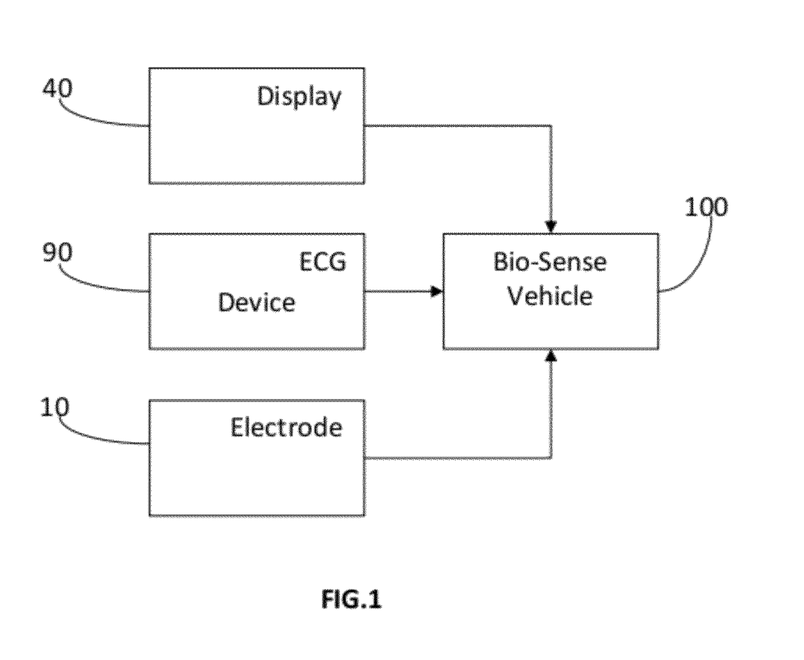
FIG. 1 illustrates the block diagram of Bio-Sensor Vehicle system setup with ECG device, Electrode and display.
Figure 4:
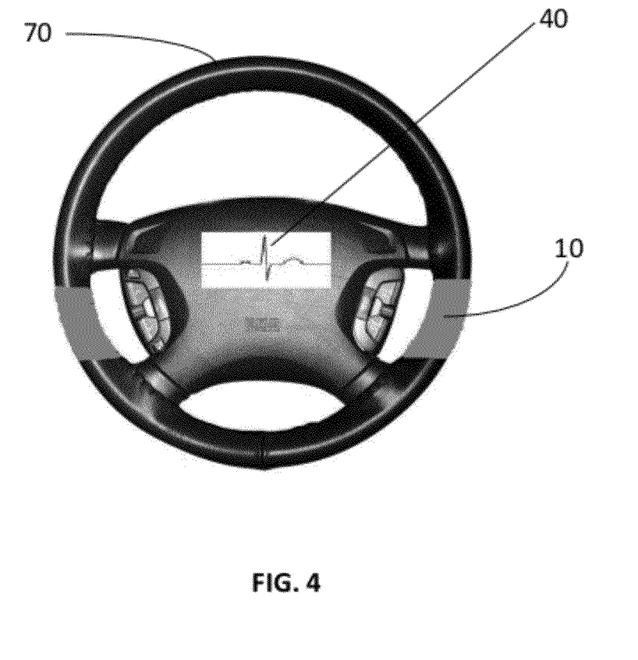
FIG. 4 shows an exemplary Bio-Sensor Vehicle system setup with ECG device, Electrode and display.

Now referring to FIGS. 1 and 4 which illustrates the biosense vehicle system setup, wherein a ECG device (90), electrode (10) and display (40) are disposed therein the vehicle. As illustrated in FIGS. 1 and 4, the In-Vehicle biosensor according to one of the exemplary embodiment comprises of a ECG device (80) is mounted at vehicle's steering wheel (70), Electrode (10) is mounted on a side bar of the steering wheel and a display (40) is disposed at the center and on top of the (90) steering wheel of vehicle to display the ECG trace, heart rate calculated from ECG trace, and sound track played in the vehicle etc.

Figure 2:
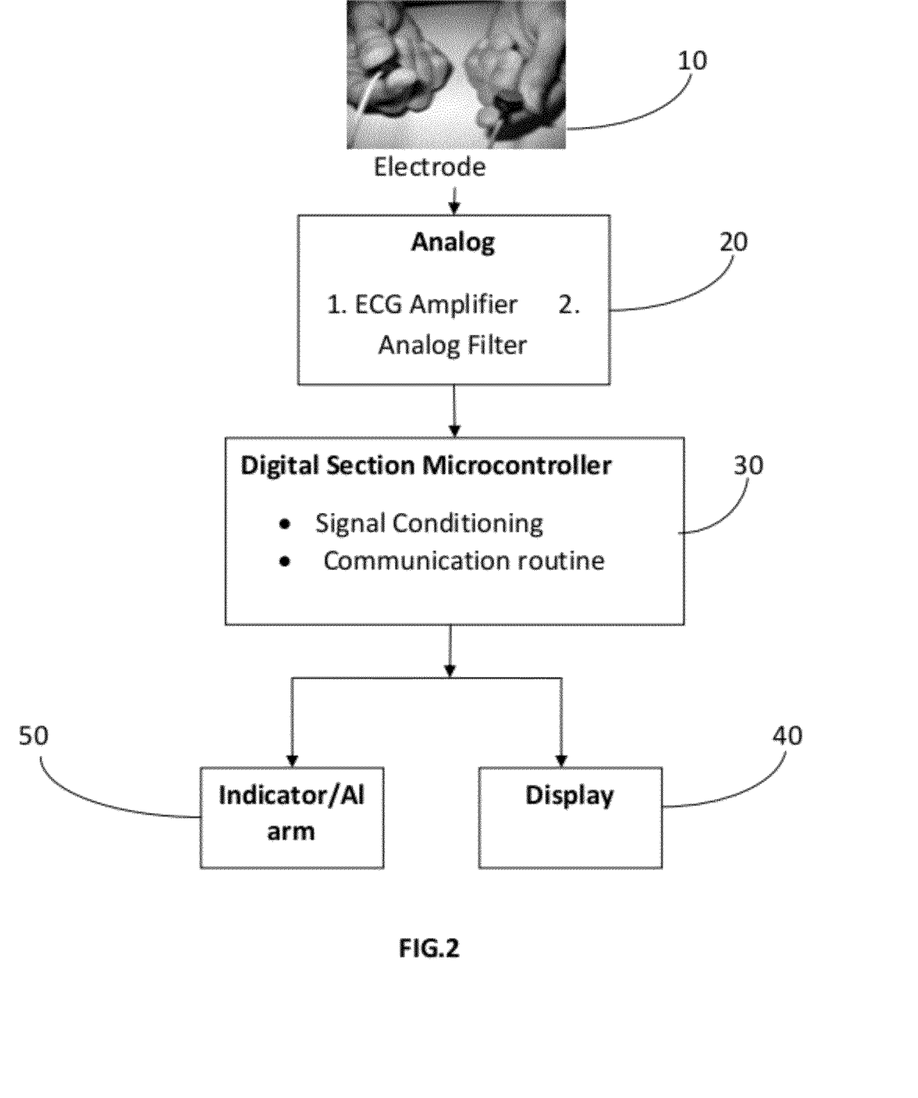
FIG. 2 illustrates a schematic block diagram of an embodiment of Bio-Sensor Vehicle system for recording and optionally displaying the cardiac signal or ECG Signal.

Referring to FIG. 2 the Electrode (10) lead is placed on the side bar of the steering wheel which measures a low voltage signal approximately 1 mV. The system of present invention adapts a single lead ECG system. Due to low voltage property of signal, the acquired ECG signal is amplified using a differential amplifier (20). Amplified signal are filtered (20) to reject the noise present in the ECG signal and to collect the decided frequencies of signal. Filtered ECG signal were passed to Digital section (30). ECG signal which is passed to the microcontroller is an input signal to ADC and is sampled at 250 Hz. Sampled ECG signals are preprocessed and feature parameter are acquired and stored for future processing. Extracted features were processed and used for two applications.

In an another embodiment of the present invention, the In-Vehicle Biosensor device is used as a single lead ECG monitoring device, which acquires single lead ECG and extract the features therefrom. The extracted features are used to calculate the heart rate and display the same. In addition to this, if any arrhythmia occurs, the digital section detected and set on the Alarm/indication as shown in FIG. 2. In addition to the status indication, it also enables the e-call to emergency unit.

Figure 5:
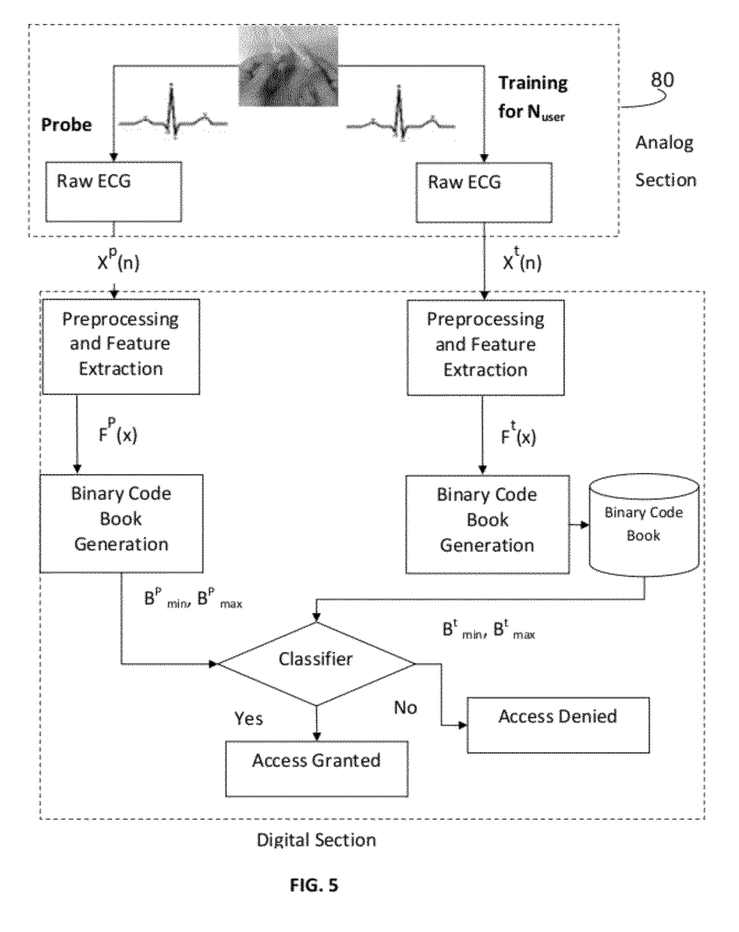
FIG. 5 illustrates the flowchart algorithm of secure person identification system of the Bio-Sensor Vehicle system.

Now referring to FIG. 5 which depicts steps for person identification in biosensor vehicle system (80), in one of the exemplary embodiments, the Electrode (10) is placed on the side bar of the steering wheel measures a low voltage signal approximately 1 mV and registers the profile of driver(s). The individual data is stored as binary code sequence which is generated from the extracted features of the ECG trace based on binary code book rules which accounts for feature variance. Whenever a driver or any person enters the vehicle the biosensors generates a binary code which is matched from the profiles already stored in the Binary code book; If profile matches then system allows entry of person in vehicle if profile does not matches system rejects the ECG signals and generates appropriate alert (50) to the concern person.

Figure 3:
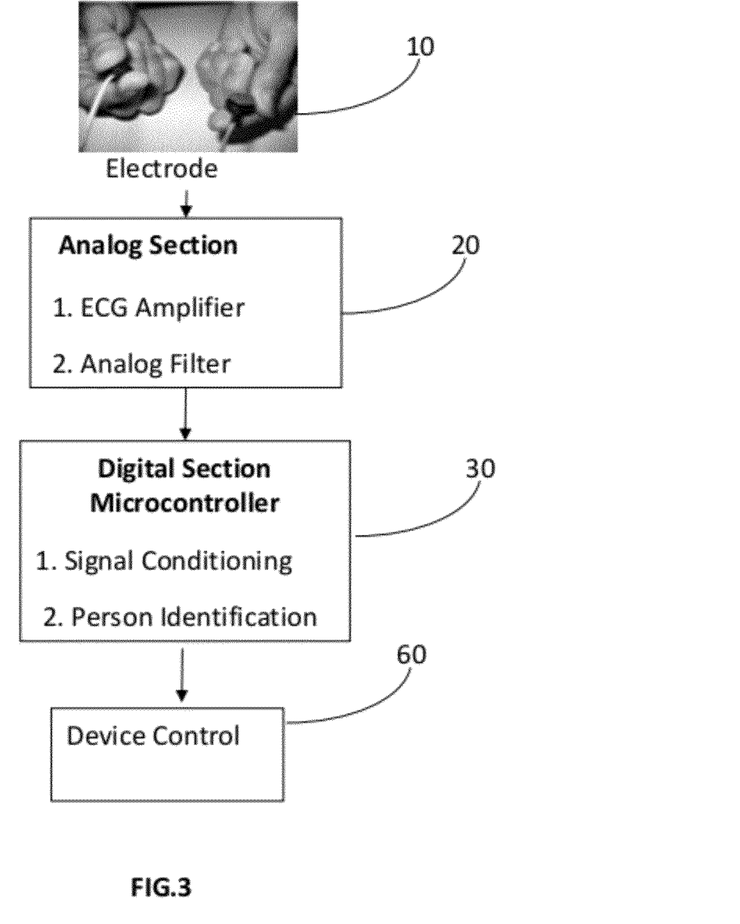
FIG. 3 shows a schematic block diagram of an embodiment of Bio-Sensor Vehicle system for person identification or biometric.

According to one of the preferred embodiments of the invention, the extracted features were used for biometric system as shown in FIGS. 3 and 5. Extracted features were converted to binary sequence using binary sequence code book generation algorithm for privacy enabled storage of the ECG. Here the original raw ECG waveform of the user is never stored in the memory. This prevents anyone from retrieving the ECG data from the vehicle electronics and using it for any other application including replay attack. In replay attack the raw ECG waveform is replayed and applied to the ECG sensor as if it is coming from a live person.

Binary Sequence Code Book Generation Algorithm:
Based on key observation of feature space a Binary code book is designed for each user which consists of variances of extracted features of the ECG trace for a particular user.
Let,
Number of users is 'U'
Number of trails for one users is 'T' and
Feature 'F' of ECG trace is of length 'N'.

$$Fmin_i(j) = \begin{cases} \frac{\min(F_i(k, j))}{10}, & \text{if } (\min(F_i(k, j)) > 9) \\ \min(F_i(k, j)), & \text{else} \end{cases}$$

$$B_{min}(i, j) = Fmin_i(j)$$

$$Fmax_i(k, j) = \begin{cases} \frac{\max(F_i(k, j))}{10}, & \text{if } (\max(F_i(k, j)) > 9) \\ \max(F_i(k, j)), & \text{else} \end{cases}$$

$$B_{max}(i, j) = Fmax_i(j)$$

where, $= 1, 2 \ldots U$
$= 1, 2 \ldots N$
$= 1, 2 \ldots T$ $B_{min}, B_{max}$ are Binary code book.

Here all the numbers are represented in 2^4 binary format.
If the test feature vector satisfies the lower bound and upper bound of users then we classify the test data feature vector accordingly. It is experimentally found that, test feature vector satisfying the boundary conditions of users will yield in a sub set of total number of users.

This method of binary code book reduce the computational time of Nearest Neighbor Classifier (NNC) when there are large number of users and hence, Binary code book is used as a first stage classifier followed by NNC at second stage.
Nearest Neighbor Classifier Algorithm:
We have used Non parametric nearest neighbor classifier as a second stage classifier which is simple yet powerful classifier. Binary code book generator (first stage classifier) resulting in subset of users is fed to the NNC to choose the closest matching user to the probe. The NNC methodology is simple and as follows, given a new test query q, we try to find the k closest training queries to it in terms of Euclidean distance.

The present invention addresses the approach of integrating the ECG sensing device in car (in-vehicle biosensor device) for monitoring the heart status and secure person identification of a driver. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. In as much as the present disclosure includes that contained in the appended claims as well as that of the foregoing description. Although this invention has been described in its preferred forms with a certain degree of particularity, it is understood that the present disclosure of the preferred form has been made only by way of example and numerous changes in the details of construction and combination and arrangement of parts may be resorted to without departing from the spirit and scope of the invention.

WORKING EXAMPLE

Step 1

The Raw ECG data of mV signal is acquired through surface electrode and amplified to Voltage signal X (n). Raw ECG signals were pre-processed and feature parameters F(X) were extracted as shown in Table 1.
where, F(X)={F1, F2 . . . . F9}

TABLE 1

| | | | ECG Features for user 1 and user 2 | | | | | | |
|---|---|---|---|---|---|---|---|---|---|
| User | F1 | F2 | F3 | F4 | F5 | F6 | F7 | F8 | F9 |
| 1 | 0.038 | 0.814 | 39.042 | 93.222 | 44.861 | 27.556 | 44.861 | 39.042 | 138.806 |
| 2 | 0.288 | 0.811 | 25.223 | 87.16 | 31.532 | 27.532 | 31.532 | 25.223 | 119.17 |

Step 2

Extracted features parameter F(x) were converted to binary sequence B (F(x)) using binary sequence code book generation algorithm as shown in Table 2

TABLE 2

| | Binary codes for user 1 and user 2 |
|---|---|
| User | Binary codes |
| 1 | 0000 0000 0111 1001 1001 0010 1001 0111 0111 |
| 2 | 0000 0000 0101 1000 0101 0101 0101 0101 0100 |

Similarly binary codes are generated for all the training set of users and a database is created.

Once we get the probe data, step 1 and 2 are performed. Later, the binary code generated from the probe is matched to the trained binary codes database using classifier or matching techniques.

For example two cases were considered, which deals with authorized and unauthorized person.

Case 1

In case-1 an authorized person, i.e. user-1 trail and the corresponding extracted features and binary codes are presented in table 3. Classifier or matching technique tries to match the binary code of probe data with trained binary codes database presented in table 2 and yields a closest matching output as user-1.

TABLE 3

| | Feature F(x) and Binary code B(F(x)) for authorized user | | | | | | | | |
|---|---|---|---|---|---|---|---|---|---|
| | F1 | F2 | F3 | F4 | F5 | F6 | F7 | F8 | F9 |
| Feature | 0.026 | 0.805 | 39.653 | 93.028 | 45.431 | 27.361 | 45.431 | 39.653 | 139.167 |
| Binary code | 0000 | 0000 | 0111 | 1001 | 1001 | 0010 | 1001 | 0111 | 0111 |

Case 2

In case-2 an unauthorized person (whose data is not present in the trained database) and his/her corresponding feature and binary code are presented in table 4. Classifier or matching technique tries to match the binary code of probe data with trained binary codes database presented in table 2. The matching/classification algorithm compares the probe data and rejects the user.

TABLE 4

| | Feature F(x) and Binary code B(F(x)) for unauthorized user | | | | | | | | |
|---|---|---|---|---|---|---|---|---|---|
| | F1 | F2 | F3 | F4 | F5 | F6 | F7 | F8 | F9 |
| Feature | 0.013 | 0.774 | 22.829 | 133.855 | 57.513 | 28.211 | 57.513 | 22.829 | 191.934 |
| Binary codes | 0000 | 0000 | 0100 | 0100 | 1001 | 0101 | 1001 | 0100 | 0100 |

ADVANTAGES OF THE INVENTION

1. The present invention monitors the cardiac status of driver in a real time fashion.
2. The present invention provides person/driver identification using ECG trace recorded by cardiac device.
3. The present invention displays the ECG trace, Heart rate, sound track to provide insights of cardiac condition.
4. The present invention also monitors other health conditions including blood pressure, skin temperature etc.
5. The present invention enables to make emergency call by providing real time diagnosis.
6. The present invention generates alerts to the subject person to an external contact point for required assistance in case of emergency.
7. The present invention automatically personalizes the vehicle based on user preferences/profile.
8. The present invention detects the entry of person/driver in the vehicle thereby prevents unauthorized entry in the vehicle.
9. The present invention provides intruder detection towards vehicle security.
10. The present invention biosensors are non intrusive and monitors the cardiac activity in a non distracting manner.
11. The present invention stores a converted binary sequence code of ECG data for biometrics.

We claim:

1. A system for identification, personalization, and monitoring cardiac activity of a driver in a vehicle, based on ECG data, the system comprising:

ECG trace probing means for acquiring in real-time one or more electric signals generated by cardiac muscles of the driver, wherein the one or more electric signals are filtered to eliminate noise, and wherein the one or more electrical signals are representative of raw ECG data of the driver;

means for extracting ECG features from the raw ECG data and converting each ECG feature into a binary code sequence using a binary sequence code book generation algorithm in a binary code book, wherein the binary code sequence of each ECG feature comprises a minimum value and a maximum value, indicating a variance in the ECG feature of the driver;

a memory storage comprising a plurality of binary code books wherein each binary code book is designated to store the binary code sequences for the extracted ECG features of an identified driver as a profile of the identified driver;

means for identifying the driver by matching real time extracted ECG features from real time raw ECG data converted to a real time binary code sequence with one of the profiles in the memory storage, wherein the real time binary code sequence of the real time extracted ECG features are matched with the binary code sequence of the raw ECG using a nearest neighbor classifier algorithm; and means for storing preferences of the driver for personalization in the vehicle, wherein the preferences are triggered in the vehicle after the binary code sequence and the enrolled binary code book sequence are matched.

2. The system of claim 1, wherein the ECG trace probing means are enabled to measure Lead ECG signal.

3. The system of claim 1, further comprising means for displaying the cardiac activity of the driver, wherein the cardiac activity is determined from the ECG data.

4. The system of claim 3, wherein the display means is mounted on either the center or top of the steering wheel.

5. The system of claim 1, wherein the system further comprises means to alert the driver in case the driver is detected with abnormal cardiac activity.

6. The system as claimed in claim 5, further comprising means for making automatic emergency call in case the alert is generated.

7. The system of claim 6, wherein the alert is signaled to a subject, person, and an external contact point for assistance as an emergency call.

8. The system of claim 1, wherein the means for identifying the driver is mounted on at least one of a steering wheel, a driver seat, or a gear.

9. The system of claim 1, wherein cardiac activities of the driver are monitored in the form of an electrocardiogram waveform and a heart rate.

10. The system of claim 1, wherein the system further comprises a probing means to determine skin temperature, respiration, stress, and blood pressure of the driver.

11. The system of claim 1, wherein the personalization comprises a plurality of user preferences including a plurality of rear view mirrors, an active play list of songs, a video and a plurality of FM/TV stations, a speaker volume, a sound level of horn, a dashboard display, a perfume fragrance, a seat height, a tilt, a plurality of climate control settings, a speed limit, a plurality of security settings, a plurality of navigation display settings, and an engine response.

12. The system of claim 1, wherein the sensor comprises a single lead ECG.

* * * * *